United States Patent
Algawi et al.

(10) Patent No.: US 11,553,937 B2
(45) Date of Patent: Jan. 17, 2023

(54) DEFLECTION MECHANISM OF AN EAR-NOSE-THROAT TOOL

(71) Applicant: BIOSENSE WEBSTER (ISRAEL) LTD., Yokneam (IL)

(72) Inventors: Yehuda Algawi, Binyamina (IL); Assaf Govari, Haifa (IL); Ilya Sitnitsky, Nahariya (IL); Stanislav Katzir, Hadera (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 151 days.

(21) Appl. No.: 16/730,772

(22) Filed: Dec. 30, 2019

(65) Prior Publication Data
US 2021/0196299 A1   Jul. 1, 2021

(51) Int. Cl.
*A61F 2/95* (2013.01)
*A61B 17/24* (2006.01)
(Continued)

(52) U.S. Cl.
CPC .......... *A61B 17/24* (2013.01); *A61B 17/3423* (2013.01); *A61B 1/05* (2013.01); *A61B 1/0684* (2013.01); *A61B 5/062* (2013.01); *A61B 5/066* (2013.01); *A61B 5/682* (2013.01); *A61B 5/6817* (2013.01); *A61B 5/6819* (2013.01); *A61B 2017/00323* (2013.01); *A61B 2017/00526* (2013.01); *A61B 2090/3762* (2016.02);
(Continued)

(58) Field of Classification Search
CPC . A61F 2/95; A61F 2/958; A61B 17/24; A61B 17/34; A61B 17/3423; A61B 2017/1205
See application file for complete search history.

(56) References Cited

U.S. PATENT DOCUMENTS 5,391,199 A  2/1995 Ben-Haim
6,239,724 B1  5/2001 Doron et al.
(Continued)

FOREIGN PATENT DOCUMENTS

EP  3395231  10/2018
WO  WO9605768  2/1996

OTHER PUBLICATIONS

International Search Report dated Mar. 17, 2021 from corresponding PCT Patent Application No. PCT/IB2020/061944.
(Continued)

*Primary Examiner* — Vi X Nguyen
(74) *Attorney, Agent, or Firm* — Frost Brown Todd LLC

(57) ABSTRACT

A medical tool includes, a deflectable distal end, at least a pull wire, and a deflection assembly. The at least pull wire having a first end coupled to the distal end of the medical tool and configured to be moved for deflecting the distal end. The deflection assembly is coupled to a second end of at least the pull wire and is configured to control a deflection of the distal end. The deflection assembly includes a first gear having a first rotation axis, and a second gear, having a second rotation axis and including a jagged surface for integrating with the first gear. The jagged surface is slanted relative to the second rotation axis, and when the first gear rotates, the second gear is configured to be rotated by the first gear, to move along the second rotation axis and to deflect the distal end by moving the pull wire.

6 Claims, 4 Drawing Sheets

(51) Int. Cl.
*A61B 17/34* (2006.01)
*A61B 90/00* (2016.01)
*A61M 1/00* (2006.01)
*A61B 1/05* (2006.01)
*A61B 1/06* (2006.01)
*A61B 5/06* (2006.01)
*A61B 5/00* (2006.01)
*A61B 17/00* (2006.01)
*A61M 25/01* (2006.01)
*A61M 25/09* (2006.01)
*A61M 25/10* (2013.01)

(52) U.S. Cl.
CPC .......... *A61M 1/84* (2021.05); *A61M 25/0136* (2013.01); *A61M 25/09* (2013.01); *A61M 25/10* (2013.01); *A61M 2025/015* (2013.01)

(56) References Cited

U.S. PATENT DOCUMENTS

| | | | |
|---|---|---|---|
| 6,332,089 B1 * | 12/2001 | Acker | A61N 7/02 128/899 |
| 6,484,118 B1 | 11/2002 | Govari | |
| 6,485,455 B1 | 11/2002 | Thompson et al. | |
| 6,618,612 B1 | 9/2003 | Acker et al. | |
| 6,690,963 B2 | 2/2004 | Ben-Haim et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2007/0156224 A1 * | 7/2007 | Cioanta | A61F 2/95 623/1.11 |
| 2011/0295242 A1 | 12/2011 | Spivey et al. | |
| 2013/0304200 A1 | 11/2013 | McLean et al. | |
| 2014/0073911 A1 | 3/2014 | Munrow et al. | |
| 2016/0287210 A1 | 10/2016 | Chumo et al. | |
| 2018/0344978 A1 | 12/2018 | Shameli et al. | |
| 2019/0015646 A1 | 1/2019 | Matlock et al. | |
| 2019/0038301 A1 | 2/2019 | Algawi et al. | |
| 2019/0374751 A1 | 12/2019 | Finson et al. | |

OTHER PUBLICATIONS

International Search Report dated Mar. 12, 2021 from corresponding PCT Patent Application No. PCT/IB2020/061566.

* cited by examiner

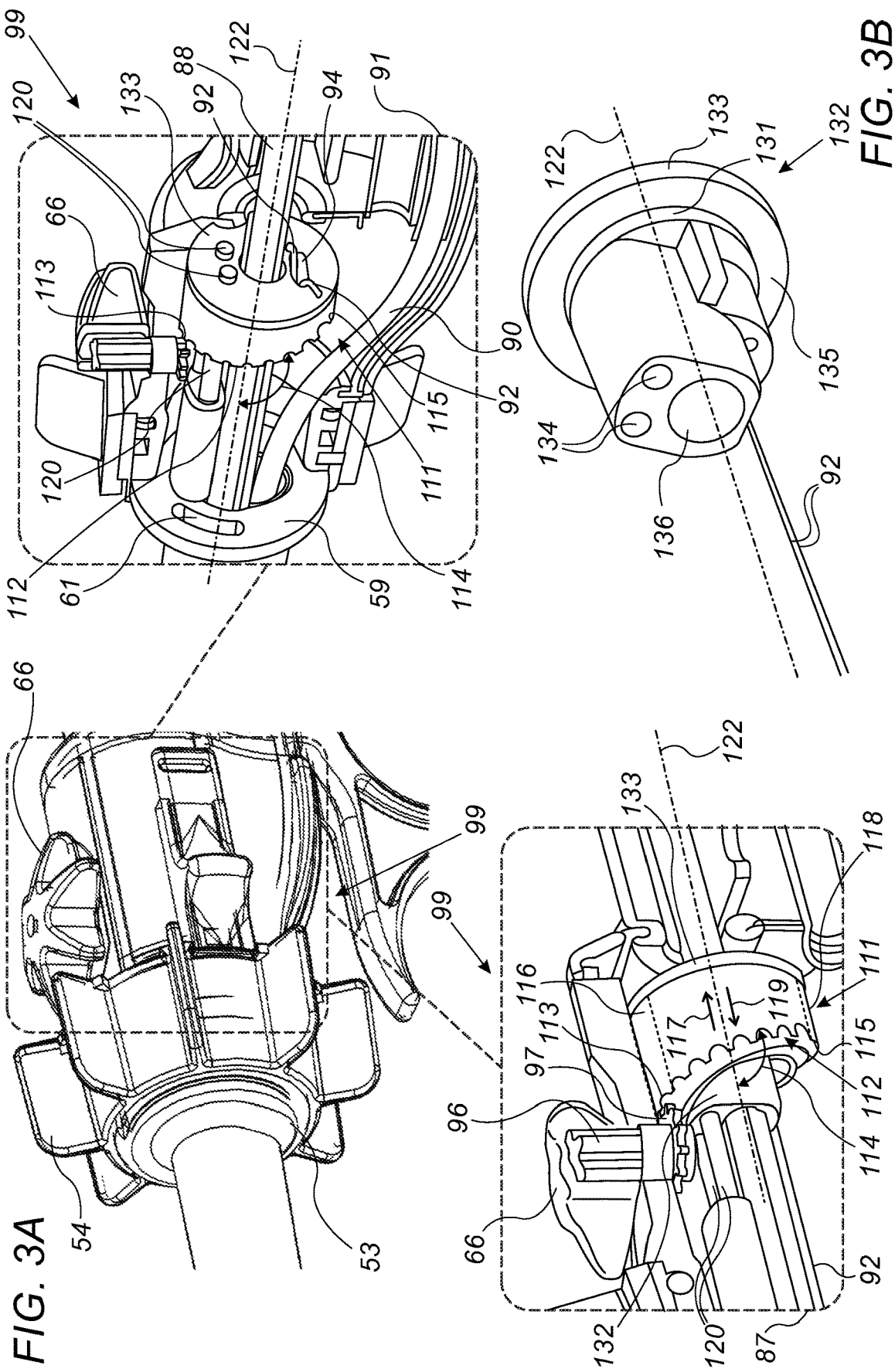

DEFLECTION MECHANISM OF AN EAR-NOSE-THROAT TOOL

CROSS-REFERENCE TO RELATED APPLICATIONS

This application is related to U.S. patent application Ser. No. 16/730,750, filed Dec. 30, 2019, published as U.S. Pub. No. 2021/0196298 on Jul. 1, 2021, and U.S. patent application Ser. No. 16/730,786, filed Dec. 30, 2019, published as U.S. Pub. No. 2021/0196930 on Jul. 1, 2021.

FIELD OF THE INVENTION

The present invention relates generally to medical devices, and particularly to methods and systems for deflecting ear-nose-throat (ENT) tools.

BACKGROUND OF THE INVENTION

Some medical tools, such as ear-nose-throat (ENT) tools, may have bending capabilities.

For example, U.S. patent application publication 2011/0295242, issued as U.S. Pat. No. 8,992,422 on Mar. 31, 2015, describes devices and systems for controlling movement of a working end of a surgical device by means of a robotic system. In one embodiment, systems and devices are provided for moving an end effector on a distal end of a surgical fastening device. Movement can include rotational movement of the end effector about an axis of the shaft, articulation of the end effector relative to the shaft, and actuation of an end effector, e.g., closing, firing, and/or cutting.

U.S. Pat. No. 6,485,455 describes a catheter having an electrode tip assembly that is bendable at the selection of the user in two different directions. The electrode tip assembly assumes different asymmetric predetermined curve configurations when bent in the two directions and is manipulated by means of steering wires adjustably connected tangentially to the lateral edges of a rotatable cam located in the catheter handle.

SUMMARY OF THE INVENTION

An embodiment of the present invention that is described herein provides a medical tool, including a rotatable hollow tube and one or more electrical wires. The rotatable hollow tube is defining a working channel therein for insertion of a medical instrument into a cavity of a patient body. The one or more electrical wires traverse the working channel for exchanging electrical signals with one or more electronic devices located at a distal end of the rotatable hollow tube. The working channel has a non-circular cross section for passing both the medical instrument and the one or more electrical wires, and for allowing rotation of the rotatable hollow tube relative to the medical instrument located inside the working channel in the presence of the one or more electrical wires.

In some embodiments, the cavity includes a nasal cavity in a head of the patient, and the medical instrument is selected from a list consisting of: (a) a balloon, (b) a guidewire, (c) a pumping tube, (d) a surgical tool, (e) an ear-nose-throat diagnostics tool, (f) an ear-nose-throat treatment tool, and (g) any combination thereof. In other embodiments, the medical tool includes a rotatable knob, which is configured to rotate at least one of the rotatable hollow tube and the medical instrument using a rotation mechanism. In yet other embodiments, the rotatable knob is configured to rotate over a range of rotation angles between 0° and 180°, in at least one of clockwise and counterclockwise rotation directions.

In an embodiment, the medical tool includes one or more pull wires, each having a first end coupled to the distal end and a second end coupled to a deflection mechanism for deflecting the distal end by pulling the one or more pull wires. The rotatable hollow tube includes retainers configured to couple between the hollow tube and the deflection mechanism so as to prevent twisting of the one or more pull wires around a component of the medical tool. In another embodiment, the one or more electrical wires include a braid of the electrical wires.

There is additionally provided, in accordance with an embodiment of the present invention, a method for producing a medical tool, the method includes providing a rotatable hollow tube that is defining a working channel therein for insertion of a medical instrument into a cavity of a patient body. One or more electrical wires are passed through the working channel for exchanging electrical signals with one or more electronic devices located at a distal end of the rotatable hollow tube. The working channel has a non-circular cross section for passing both the medical instrument and the one or more electrical wires, and for allowing rotation of the rotatable hollow tube relative to the medical instrument that is located inside the working channel in the presence of the one or more electrical wires.

Another embodiment of the present invention provides a medical tool, including a distal end that is deflectable, at least a pull wire, and a deflection assembly. The at least pull wire having a first end coupled to the distal end of the medical tool and configured to be moved for deflecting the distal end. The deflection assembly is coupled to a second end of at least the pull wire and is configured to control a deflection of the distal end. The deflection assembly includes a first gear having a first rotation axis, and a second gear, having a second rotation axis and including a jagged surface for integrating with the first gear. The jagged surface is slanted relative to the second rotation axis, and when the first gear rotates, the second gear is configured to be rotated by the first gear and to move along the second rotation axis and to deflect the distal end by moving the pull wire.

In some embodiments, the second gear has a circumference including: (i) a first section having (a) a first thickness along the second rotation axis and (b) a first jagged section of the jagged surface extending therefrom, and (ii) a second section having (a) a second thickness along the second rotation axis, smaller than the first thickness and (b) a second jagged section of the jagged surface extending therefrom. When the second gear is rotated: when the first jagged section is in contact with the first gear, the distal end is deflected by a first amount, and when the second jagged section is in contact with the first gear, the distal end is deflected by a second amount, smaller than the first amount. In other embodiments, the medical tool includes a rotatable knob, which is coupled to the first gear and is configured to control the deflection by rotating the first gear. In yet other embodiments, the medical tool includes a coupling element, which is coupled to the second end of at least the pull wire, and is configured to by moved, by the second gear, along the second rotation axis.

In an embodiment, the second gear is hollow, and the medical tool includes one or more rods, which are parallel to the second rotation axis and traverse through the second gear so that the second gear is moved by the one or more rods along the second rotation axis. In another embodiment, the medical tool includes a hollow tube, disposed between the distal end and the deflection assembly, and the hollow tube defines a working channel therein for insertion of a medical instrument, through the distal end, into a cavity of a patient body. In yet another embodiment, the cavity includes a nasal cavity in a head of the patient, and the working channel is for inserting the medical instrument that is selected from a list consisting of: (a) a balloon, (b) a guidewire, (c) a pumping tube, (d) a surgical tool, (e) an ear-nose-throat diagnostics tool, (f) an ear-nose-throat treatment tool, and (g) any combination thereof.

There is additionally provided, in accordance with an embodiment of the present invention, a method for producing a medical tool, the method includes providing a distal end that is deflectable. The distal end of the medical tool is coupled to a first end of at least a pull wire to be moved for deflecting the distal end. A second end of at least the pull wire is coupled to a deflection assembly, for controlling a deflection of the distal end. The deflection assembly includes a first gear having a first rotation axis, and a second gear having a second rotation axis and including a jagged surface for integrating with the first gear. The jagged surface is slanted relative to the second rotation axis, and when the first gear rotates, the second gear is rotated by the first gear and moved along the second rotation axis for deflecting the distal end by moving the pull wire.

Another embodiment of the present invention provides a medical tool, including a deflectable distal end, at least a pull wire, and a coupling element. The at least pull wire has a first end coupled to the distal end of the medical tool, and configured to be moved for deflecting the distal end. The coupling element is coupled to a second end of the pull wire and having at least two boreholes configured to receive at least two respective rods traversing therethrough. The coupling element is configured to be moved along a rotation axis of a rotatable element coupled thereto, and the boreholes and the respective rods are configured to prevent rotation of the coupling element.

In some embodiments, the coupling element has at least an additional borehole, and the pull wire traverses through the additional borehole. In other embodiments, the rotatable element includes a hollow gear surrounding at least part of the coupling element, and when the hollow gear rotates, the coupling element is moved along the rotation axis and the rods prevent rotation of the coupling element with the hollow gear. In yet other embodiments, the coupling element has a panel, which is coupled to the second end of the pull wire and is in physical contact with the rotatable element so as to be moved along the rotation axis.

In an embodiment, the coupling element has a further borehole defining a working channel therein for insertion of a medical instrument into a cavity of a patient body. In another embodiment, the cavity includes a nasal cavity in a head of the patient, and the medical instrument is selected from a list consisting of: (a) a balloon, (b) a guidewire, (c) a pumping tube, (d) a surgical tool, (e) an ear-nose-throat diagnostics tool, (f) an ear-nose-throat treatment tool, and (g) any combination thereof.

There is additionally provided, in accordance with an embodiment of the present invention, a method for producing a medical tool, the method includes providing a distal end that is deflectable. A first end of at least a pull wire, to be moved for deflecting the distal end, is coupled to the distal end of the medical tool. A coupling element having at least two boreholes, is coupled to a second end of the pull wire, and at least two respective rods are inserted for traversing through the at least two boreholes. A rotatable element, for moving the coupling element along a rotation axis of the rotatable element, is coupled to the coupling element, so that the boreholes and the respective rods prevent rotation of the coupling element.

The present invention will be more fully understood from the following detailed description of the embodiments thereof, taken together with the drawings in which:

BRIEF DESCRIPTION OF THE DRAWINGS

FIG. 3A is a schematic, pictorial illustration of a deflection mechanism of a distal-end assembly, in accordance with an embodiment of the present invention;

FIG. 3B is a schematic, pictorial illustration of a wire holder, in accordance with an embodiment of the present invention.

DETAILED DESCRIPTION OF EMBODIMENTS

Overview

Figure 1:
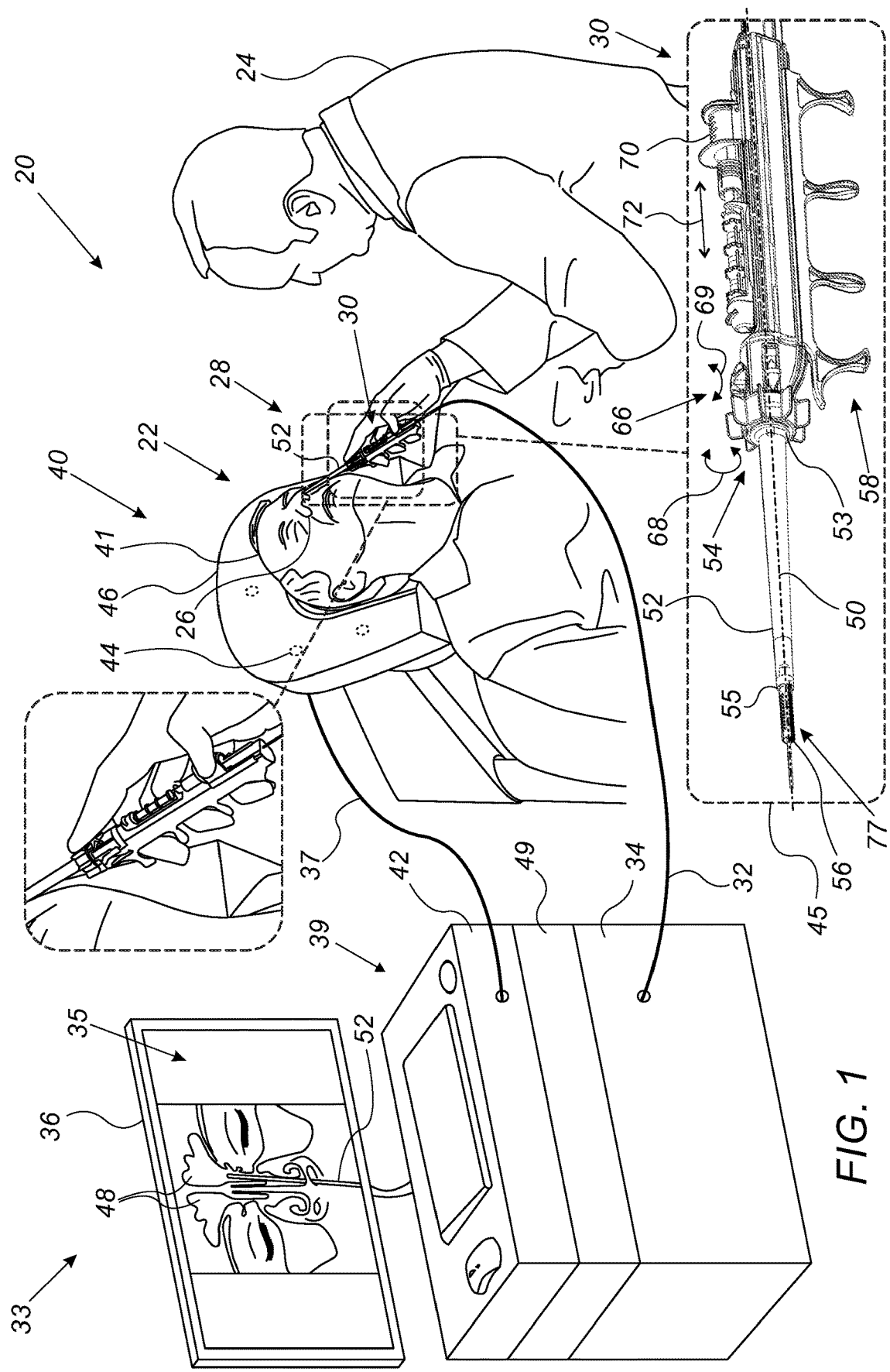
FIG. 1 is a schematic, pictorial illustration of an ear-nose-throat (ENT) procedure using an ENT system, in accordance with an embodiment of the present invention.

Some medical procedures require insertion of a medical tool into a branched organ of a patient. For example, a balloon sinuplasty procedure comprises insertion of a guidewire into a sinus of a patient ear-nose-throat (ENT) and moving a balloon on the guidewire into an ostium of the sinus so as to open an obstruction in the ostium. In other procedures a physician may insert a pumping tube for drawing mucus out of the sinus, or a surgical tool for cutting tissue (e.g., cartilage, bone, or polyp) in the patient ENT organs.

Embodiments of the present invention that are described hereinbelow provide methods and apparatus for improving the functionality and maneuverability of ENT tools. In some embodiments, an ENT system comprises an ENT tool and a control console. The ENT tool comprises a distal end inserted by a physician into a branched organ, such as the patient sinus. The ENT tool comprises a rotatable hollow tube defining a working channel for inserting into the sinus medical instruments, such as but not limited to the aforementioned guidewire, balloon, pumping tube, surgical tool, or any combination thereof.

In some embodiments, the ENT tool comprises rotation and deflection mechanisms for improved maneuvering of the distal end and for insertion of the aforementioned instruments into the sinus. The ENT tool comprises electronic devices, such as a camera and light emitting diodes (LEDs) coupled to the distal end and configured to acquire images of the tissue in question. In some embodiments, the ENT system comprises one or more electrical wires, typically incorporated in a braid passing through the working channel, and configured to exchange electrical power and imaging signals between the console and the electronic devices at the distal end.

During an ENT procedure, the physician rotates and/or deflects at the distal end of the ENT tool having, in the working channel, one or more of the medical instruments and the braid of electrical wires. In some cases, the braid may be winded around a medical instrument, and may be teared and/or interfere with the motion of the medical instrument.

In some embodiments, the working channel has a non-circular cross section for passing both the medical instrument and the braid of electrical wires, and to allow rotation of the medical instrument relative to the hollow tube in the presence of the braid of electrical wires.

In some embodiments, the ENT tool comprises a rotatable knob, which is configured to rotate at least one of the rotatable hollow tube and the medical instrument. The rotatable knob is configured to rotate clockwise and counterclockwise over a range of rotation angles between 0° and 180°.

In some embodiments, the ENT tool comprises one or more pull wires having (a) a distal end coupled to the distal end the ENT tool, and (b) a proximal end coupled to the deflection mechanism, also referred to herein as a deflection assembly, of the ENT tool. In some embodiments, the deflection assembly comprises (i) a first gear, configured to rotate about a first rotation axis and controlled by a deflection knob operated by the physician, and (ii) a second gear, rotating about a second rotation axis and comprising a jagged surface for integrating with the first gear. The jagged surface is slanted relative to the second rotation axis, and when the physician rotates the deflection knob, the second gear is rotated by the first gear and is moved along the second rotation axis, so as to deflect the distal end by moving the pull wire.

In some embodiments, the ENT tool comprises a wire holder, also referred to herein as a coupling element, which makes a physical contact with the second gear, and which is coupled to the proximal end of the one or more pull wires. In such embodiments, the wire holder is configured to by moved, by the second gear, along the second rotation axis.

The physical contact between the wire holder and the second gear may cause rotation of the wire holder together with the second gear, which may result in twisting of the pull wires around one another and/or around other elements of the ENT tool. In some embodiments, the wire holder has at least two boreholes configured to receive at least two respective rods traversing therethrough. In such embodiments, the boreholes and rods are configured to prevent rotation of the coupling element, thus, preventing twisting of the pull wires.

In some embodiments, the pull wire may have additional boreholes for traversing various components of the ENT tool, such as but not limited to one or more of the medical instruments, and the aforementioned pull wires.

The disclosed techniques improve the functionality of medical tools by enabling simultaneous operation of multiple diagnostics and/or treatment devices by a single physician. Moreover, the disclosed techniques improve the maneuverability of such multifunctional medical tools in various branched organs, such as ENT, bronchoscopy, or neurology procedures, but may require adjustments of the configuration for specific applications.

System Description

FIG. 1 is a schematic, pictorial illustration of an ear-nose-throat (ENT) procedure using an ENT system 20, in accordance with an embodiment of the present invention. In some embodiments, the ENT procedure may comprise a balloon sinuplasty procedure in which a balloon is inserted into a blocked ostium of a sinus 48, and is inflated so as to open the ostium for enabling a regular flow and evacuation of mucus from the sinus through a nasal cavity of a nose 26 of a patient 22. In other embodiments, the ENT procedure may comprise any other diagnostic or treatment procedure carried out in the patient ENT. In such embodiments, ENT system 20 comprises a medical catheter, in the present example an ENT tool 28, which is configured to carry out one or more of the ENT procedures in one or more sinuses 48 of patient 22.

In some embodiments, ENT tool 28 comprises a rotatable hollow tube, referred to herein as a tube 52, which is inserted, by a physician 24, into a cavity, such as the aforementioned nasal cavity of nose 26, of patient 22. ENT tool 28 further comprises a handheld apparatus 30, coupled to a proximal end of tube 52 and configured to assist physician 24 to carry out the ENT procedure in a head 41 of patient 22 as will be described in detail below.

Reference is now made to an inset 45. In some embodiments, ENT tool 28 comprises a distal-end assembly 77, which is coupled to a distal end of tube 52. Distal-end assembly 77 may comprise a nickel-titanium alloy, such as Nitinol™, or any other suitable material, and is configured to be deflected and rotated as will be described in detail below.

In some embodiments, handheld apparatus 30 comprises a gripper 58 held by the fingers of physician 24. In some embodiments, handheld apparatus 30 comprises a slider 70 that is moved along a longitudinal axis of ENT tool 28, by the thumb of physician 24. In the example of inset 45 physician 24 moves slider 70 in two directions shown as a double-headed arrow 72, so as to insert and/or retract medical instruments, such as a balloon (not shown), into and/or out of head 41 of patient 22.

Reference is now made back to the general view of FIG. 1. In an embodiment, system 20 further comprises a magnetic position tracking system, which is configured to track the position of one or more position sensors in head 41. The magnetic position tracking system comprises magnetic field-generators 44 and a position sensor 55, which generates position signals in response to sensing external magnetic fields generated by field-generators 44, thereby enabling a processor 34 (described in detail below) to estimate the position of position sensor 55 within head 41 of patient 22.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1 issued as U.S. Pat. No. 7,729,742 on Jun. 1, 2010; and 2004/0068178 A1, now abandoned, whose disclosures are all incorporated herein by reference.

In some embodiments, system 20 further comprises a location pad 40, which comprises field-generators 44 fixed on a frame 46. In the exemplary configuration shown in FIG. 1, pad 40 comprises five field-generators 44, but may alternatively comprise any other suitable number of field-generators 44. Pad 40 further comprises a pillow (not shown) placed under head 41 of patient 22, such that field-generators 44 are located at fixed and known positions external to head 41.

In some embodiments, system 20 comprises a console 33, which comprises a memory 49, and a driver circuit 42 configured to drive, via a cable 37, field-generators 44 with suitable signals so as to generate magnetic fields in a predefined working volume in space around head 41.

In some embodiments, console 33 comprises processor 34, typically a general-purpose computer, with suitable front end and interface circuits for receiving signals from ENT tool 28 having one or more magnetic sensors 55 coupled thereto, via a cable 32, and for controlling other components of system 20 described herein.

In some embodiments, processor 34 is configured to estimate the position of each position sensor 55. Based on the estimated positions of the respective sensors, in the coordinate system of the magnetic position tracking system, processor 34 is configured to derive the position, orientation and radius of curvature of distal-end assembly 77.

In the context of the present invention and in the claims, the terms "bending" "deflecting" are used interchangeably and refer to steering of one or more sections of ENT tool 28.

In some embodiments, processor 34 is configured to receive via an interface (not shown), one or more anatomical images, such as computerized tomography (CT) images depicting respective segmented two-dimensional (2D) slices of head 41, obtained using an external CT system (not shown). The term "segmented" refers to displaying various types of tissues identified in each slice by measuring respective attenuation of the tissues in the CT system.

Console 33 further comprises input devices 39 for controlling the operation of system 20, and a user display 36, which is configured to display the data (e.g., images) received from processor 34 and/or to display inputs inserted by physician 24 or another user of input devices 39.

In some embodiments, processor 34 is configured to select one or mode slices from among the CT images, such as an anatomical image 35, and to display the selected slice on user display 36. In the example of FIG. 1, anatomical image 35 depicts a sectional front-view of one or more sinuses 48 of patient 22.

In some embodiments, processor 34 is configured to register between the coordinate systems of the CT system and the magnetic position tracking system, and to overlay the position of distal-end assembly 77, on anatomical image 35.

Reference is now made back to inset 45. In some embodiments, handheld apparatus 30 comprises a deflection knob, referred to herein as a knob 66, which is controlled by physician 24 and is configured to deflect distal-end assembly 77 by rotating about its axis clockwise and counterclockwise as shown by a double-headed arrow 69.

In some embodiments, handheld apparatus 30 further comprises a rotation knob, referred to herein as a knob 54, which is configured to rotate clockwise and counterclockwise as shown by a double-headed arrow 68, so as to rotate at least one of tube 52, distal-end assembly 77, and a medical instrument (shown in FIGS. 2A, 2B, 3A and 3B below) within tube 52, about longitudinal axis 50. In the present example, knob 54 rotates both tube 52 and distal-end assembly 77 about longitudinal axis 50, whereas the medical instrument is not rotated. In some embodiments, knob 54 is configured to be rotated 180° clockwise and 180° counterclockwise as will be described in detail in FIGS. 2A and 2B below.

In some embodiments, distal-end assembly 77 comprises electronic devices 56, such as but not limited to a camera and one or more light-emitting diodes (LEDs). Electronic devices 56 are coupled to the distal end of distal-end assembly 77 and are configured to illuminate the ENT tissue in question and to acquire anatomical images of the ENT tissue during the ENT procedure.

Reference is now made back to the general view of FIG. 1. Note that FIG. 1 shows only elements related to the disclosed techniques, for the sake of simplicity and clarity. System 20 typically comprises additional modules and elements that are not directly related to the disclosed techniques, and therefore, are intentionally omitted from FIG. 1 and from the description of system 20.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

This particular configuration of ENT tool 28 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example ENT tool, and the principles described herein may similarly be applied to other sorts of medical diagnostics and/or treatment tools and/or systems.

Figure 2A:
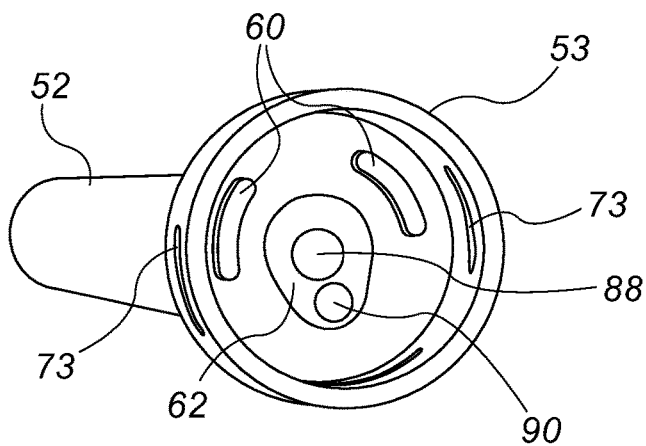
FIG. 2A is a schematic, pictorial illustration of a rotatable hollow tube, in accordance with an embodiment of the present invention.

A Rotatable Hollow Tube Having a Working Channel with a Non-Circular Cross Section FIG. 2A is a schematic, pictorial illustration of rotatable hollow tube 52, in accordance with an embodiment of the present invention. In some embodiments, rotatable hollow tube 52 defines a working channel (WC) 62 therein for insertion of a medical instrument 88 into sinus 48 (or into any other cavity) of patient 22. In some embodiments, medical instrument 88 may comprise (a) a balloon or another instrument moved along a guidewire to carry out the sinuplasty procedure described in FIG. 1 above, (b) a pumping tube coupled to a pump for drawing the patient mucus e.g., after opening the blocked ostium, (c) any suitable type of an ENT surgical tool, e.g., for cutting polyps or for removing other tissue of patient 22, (d) an ear-nose-throat diagnostics tool, (e) an ear-nose-throat treatment tool (f) any other suitable type of an ENT medical instrument, or (g) any suitable combination thereof. Note that in FIG. 2A medical instrument 88 is shown schematically in a cross section and may have any suitable size and shape.

In some embodiments, when at least distal-end assembly 77 is inserted into a nasal cavity of nose 26, physician 24 applies slider 70 for inserting medical instrument 88 (e.g., the aforementioned sinuplasty balloon) into the target tissue, such as sinus 48.

In some embodiments, system 20 comprises one or more electrical wires, in the present example a braid 90 of electrical wires that traverse WC 62 for exchanging electrical signals between console 33 and one or more electronic devices 56.

In some embodiments, the rotation of tube 52 by knob 54 is limited to 180° clockwise and 180° counterclockwise, so as to prevent winding of braid 90 around medical instrument 88. In case the rotation is not limited, the winding may result in tearing or damaging of at least one electrical wire and/or in difficulties to move medical instrument 88.

In some embodiments, WC 62 has a non-circular cross section for passing therethrough (a) one and more medical instruments 88 and (b) braid 90. The non-circular shape of WC allows the rotation of tube 52 relative to medical instrument 88 (positioned inside WC 62) in the presence of braid 90. In some embodiments, at least one of medical instrument 88 and tube 52 are configured to rotate about axis 50. In such embodiments, the non-circular cross-sectional shape of WC 62 enables the relative rotation between medical instrument 88 and tube 52, without winding one or more electrical wires of braid 90 around medical instrument 88.

In some embodiments, the proximal end of WC 62 may have the aforementioned non-circular cross-sectional shape, and the distal end of WC 62 may have any other cross-section, such as but not limited to a circular or a non-circular cross-sectional shape.

In some embodiments, tube 52 is coupled to a housing 53, in the example of system 20 housing 53 is integrated with tube 52 as a single molded piece. In other configurations tube 52 may be coupled to housing 53 using any suitable technique.

In some embodiments, housing 53 has one or more retainers 60, configured to retain housing 53 attached to at least one of a rotation mechanism shown in FIG. 2B below, and a deflection mechanism shown and described in detail in FIG. 3A below. In such embodiments, when physician 24 rotates knob 54, retainers 60 prevents twisting of pull wires (shown in FIGS. 3A and 3B below) by retaining the pull wires rotating together with tube 52.

In some embodiments, housing 53 has one or more openings 73, configured to retain housing 53 attached to knob 54 and to the aforementioned rotation mechanism.

Figure 2B:
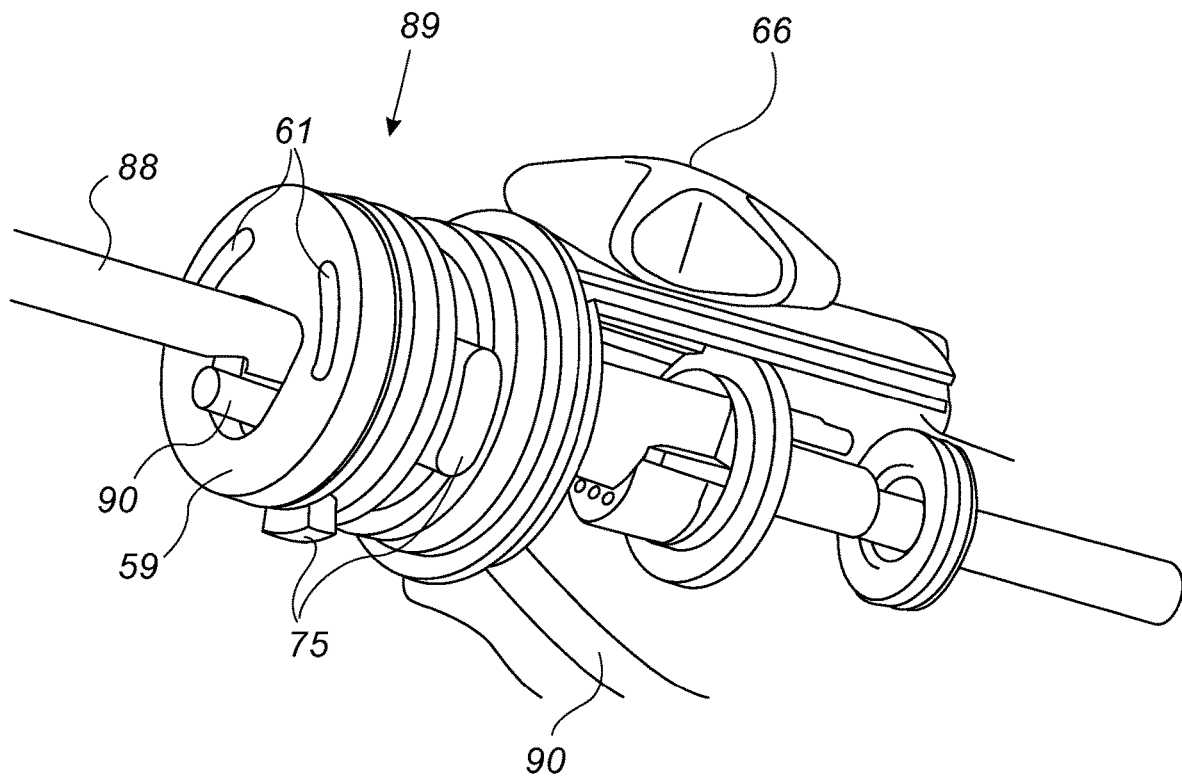
FIG. 2B is a schematic, pictorial illustration of a rotation mechanism of an ENT tool, in accordance with an embodiment of the present invention.

FIG. 2B is a schematic, pictorial illustration of a rotation mechanism 89 of tube 52 and distal-end assembly 77, in accordance with an embodiment of the present invention. In the example of FIG. 2B, several components of ENT tool 28, such as knob 54, housing 53 and tube 52, were removed from the drawing for the sake of conceptual clarity, so as to show elements of rotation mechanism 89 that are typically hidden from a viewer when ENT tool 28 is assembled.

In some embodiments, rotation mechanism 89 is configured to snugly fit in housing 53. In some embodiments, rotation mechanism 89 comprises a disc 59 having a non-circular opening surrounding medical instrument 88 and braid 90. In some embodiments, the shape of the non-circular opening is typically similar to that of WC 62, but in other embodiments the opening may have any other suitable shape.

In some embodiments, rotation mechanism 89 has one or more openings 61, each of which is configured to fit over a corresponding retainer 60 (shown in FIG. 2A above) so as to retain housing 53 attached to and rotating with rotation mechanism 89 and to retain the pull wires (shown in FIGS. 3A and 3B below) rotating together with tube 52. This configuration prevents twisting of the pull wires around one another and/or around other components of ENT tool 28, such as medical instrument 88 and/or braid 90.

In some embodiments, rotation mechanism 89 comprises one or more protrusions 75, each of which configured to fit in a corresponding opening 73 so as to couple between housing 53 and rotation mechanism 89. In such embodiments, housing 53 and tube 52 are fitted over rotation mechanism 89 so that physician 24 can insert medical instrument 88 through WC 62 defined in tube 52 and into the cavity of interest (e.g., sinus 48) of patient 22.

In some embodiments, rotation mechanism 89 is coupled to knob 54 for rotating at least one of tube 52, distal-end assembly 77, and medical instrument 88, about longitudinal axis 50 of ENT tool 28. In the present example, physician 24 applies knob 54 for rotating tube 52 and distal end assembly 77 about longitudinal axis 50.

The particular configuration of rotation mechanism 89, tube 52 and housing 53 is provided by way of example, in order to illustrate certain problems, such as enabling improved control of rotating at least one of tube 52, distal-end assembly 77, and medical instrument 88, by physician 24, which is typically during one or more of the aforementioned ENT procedures. Such problems are addressed by embodiments of the present invention and the configuration described above demonstrates the application of these embodiments in enhancing the performance of such an ENT system. Embodiments of the present invention, however, are by no means limited to this specific sort of example system, and the principles described herein may similarly be applied to other sorts of rotatable ENT and medical systems.

Deflection Mechanism for ENT Tool

FIG. 3A is a schematic, pictorial illustration of a deflection mechanism 99 of distal-end assembly 77, in accordance with an embodiment of the present invention. In some embodiments, deflection mechanism 99 is activated by knob 66 operated by physician 24. In the context of the present disclosure and in the claims, the terms "deflection mechanism" and "deflection assembly" are used interchangeably.

Reference is now made to an inset 87 showing a perspective view of deflection mechanism 99 from the distal end of ENT tool 28. In some embodiments, deflection mechanism 99 comprises a gear 96, which is coupled to and is rotated by knob 66. Gear 96 comprises a jagged surface which is integrated with a jagged surface 112 of a gear 111. In the exemplary configuration of deflection mechanism 99, gear 111 is hollow and is configured to rotate about a rotation axis 122. In the present example, rotation axis 122 is substantially parallel to longitudinal axis 50 of ENT tool 28, and is substantially orthogonal to the rotation axis of knob 66 and gear 96. In other embodiments, the rotation axes of gears 96 and 111 may have any other suitable orientation angle therebetween, different than a right angle in the present exemplary configuration. In alternative embodiments, rotation axis 122 may have any suitable orientation relative to longitudinal axis 50, e.g., not parallel.

In some embodiments, ENT tool 28 comprises one or more pull wires 92, having a first end coupled to distal-end assembly 77 and a second end coupled to deflection mechanism 99 as will be described below. At least one of pull wires 92 may have any suitable diameter between about 0.1 mm and about 0.5 mm, and may comprise stainless steel, nano-silk also referred to as spider dragline silk, aramids such as Kevlar™, or any other suitable material having a tensile strength larger than about 10 kgf. Note that the diameter of pull wires 92 is selected based on the specified range of tensile strength and forces applied to pull wires 92 for deflecting distal-end assembly 77. In some embodiments, pull wires are configured to be moved by deflection mechanism 99 for deflecting distal-end assembly 77.

In the context of the present disclosure and in the claims, the terms "about" or "approximately" for any numerical values or ranges indicate a suitable dimensional tolerance that allows the part or collection of components to function for its intended purpose as described herein. For example, "about" or "approximately" may refer to the range of values±20% of the recited value, e.g. "about 90%" may refer to the range of values from 72% to 100%.

In some embodiments, deflection mechanism 99 is configured to control the deflection of distal-end assembly 77 based on the engagement between gears 96 and 111.

In some embodiments, gear 111 is hollow so that pull wires 92 and one or more rods 120 (in the present example two rods 120) are passing therethrough. In some embodiments, jagged surface 112 is slanted relative to rotation axis 122 and defines a slant angle 114 between jagged surface 112 and rotation axis 122.

In some embodiments, slant angle 114 may have any suitable angle so as to obtain a movement of gear 111 at an exemplary range between about 1 mm and about 12 mm.

In some embodiments, ENT tool 28 comprises a wire holder 132 having a panel 133 and additional elements described in detail in FIG. 3B below. Gear 111 rotates around wire holder 132 and may have a physical contact with panel 133 of wire holder 132. As will be described in detail below, rods 120, medical instrument 88 and pull wires 92 are all passing through boreholes of wire holder 132.

In some embodiments, gear 111 has a circumference that may be laid out in parallel to rotation axis 122. Gear 111 has sections 116 and 118 located at different positions of the circumference of gear 111. In such embodiments, each section from among sections 116 and 118 is configured to make a physical contact with panel 133 and has a section of jagged surface 112. In such embodiments, a jagged section 113 of jagged surface 112 is extending from section 116, and a jagged section 115 of jagged surface 112 is extending from section 118. Note that in the configuration of deflection mechanism 99, panel 133 is not rotatable as will be described in FIG. 3B below. As shown in inset 87, due to the shape of gear 111, the thickness of section 116 along rotation axis 122 is larger than the thickness of section 118.

In some embodiments, when physician 24 rotates gear 96 by knob 66, jagged surfaces 97 and 112 are integrated with one another and gear 111 is configured to be rotated, about rotation axis 122, by gear 96 that is rotating but is not translated relative to knob 66.

In such embodiments, when jagged section 113 is in contact with jagged surface 97 of gear 96, gear 111 is configured to move along rotation axis 122, in a direction 117, and to deflect distal-end assembly 77 by a maximal amount by moving pull wires 92 as will be described below. Similarly, when jagged section 115 is in contact with jagged surfaces 97, gear 111 is configured to move along rotation axis 122, in a direction 119 and to enable straightening of distal-end assembly 77. Moreover, physician 24 may control the amount of deflection of distal-end assembly 77 by rotating knob 66 such that any other jagged section of gear 111 is in contact with jagged surface 97 of gear 96. For example, physician 24 may obtain a partial deflection of distal-end assembly 77 by rotating knob 66 such that a given jagged surface, located between jagged sections 113 and 115, is in contact with jagged surface 97 of gear 96. Note that the amount of deflection when the given jagged surface is in contact with jagged surface 97, is smaller than the amount of deflection when jagged section 113 is in contact with jagged surface 97.

As described in FIG. 1 above, distal-end assembly 77 may comprise Nitinol™ that acts as a spring when deflected. In other words, when distal-end assembly 77 is deflected, the nickel-titanium alloy applies force to pull wires 92 so as to return to a straightened (i.e., not deflected) position.

In some embodiments, when jagged section 113 is integrated with jagged surface 97 of gear 96, pull wires 92 are moved with gear 111 in direction 117 and hold distal-end assembly 77 in a deflected position. When jagged section 115 (of section 118) is integrated with jagged surface 97, pull wires 92 are moved with gear 111 in direction 119 and may be loosen so as to let the inner force of the Nitinol™ to straighten distal-end assembly 77 to a non-deflective position. Note that rods 120 serve as a rail for the motion of gear 111 in directions 117 and 119.

Reference is now made to an inset 91 showing a perspective view of deflection mechanism 99 from the proximal end of ENT tool 28. As described in inset 87 above, jagged surface 112 is slanted relative to rotation axis 122 as shown by slant angle 114.

As described in inset 87 above, rods 120, medical instrument 88 and pull wires 92 are all passing through boreholes of wire holder 132. As shown in inset 91, rods 120, medical instrument 88 and pull wires 92 protrude through panel 133, and one or more pull wires 92 are passing through a borehole 94 and are coupled to the outer surface of panel 133.

In some embodiments, rods 120 serve as a rail for the motion of wire holder 132 and gear 111 along rotation axis 122. When physician 24 rotates knob 66, rods 120 are configured to prevent panel 133 of wire holder 132 from rotating together with gear 111, and yet enable the movement of pull wires 92 along rotation axis 122 for controlling the deflection of distal-end assembly 77, as described above.

The configuration of deflection mechanism 99 is shown by way of example and incorporates interfaces with rods 120, medical instrument 88 and pull wires 92 to enable the deflection of distal-end assembly 77. Embodiments of the present invention, however, are by no means limited to this specific sort of example configuration, and the principles described herein may similarly be applied to other sorts of deflection mechanisms used in other types of medical tools and/or systems or other types of deflectable devices.

Preventing Twisting of Pull Wires when Deflecting Distal-End Assembly

FIG. 3B is a schematic, pictorial illustration of wire holder 132, in accordance with an embodiment of the present invention. In some embodiments, wire holder 132, also referred to herein as a coupling element, has boreholes 134 for passing rods 120 therethrough. In the exemplary configuration of FIGS. 3A and 3B, ENT tool 28 comprises two rods 120 and therefore wire holder 132 has two boreholes 134. In other embodiments, ENT tool 28 may have any other suitable number of one or more rods 120 and respective one or more boreholes 134.

In some embodiments, wire holder 132 has a borehole 136 defining a working channel, such as WC 62, for passing medical instrument 88 therethrough. In other embodiments, wire holder 132 may comprise multiple boreholes 136 for passing therethrough a plurality of medical instruments 88, respectively. Additionally or alternatively, boreholes may have any suitable cross section that may vary in size, shape or in any other parameters thereof.

As shown and described in inset 91 of FIG. 3A above, wire holder 132 has borehole 94 (not shown in FIG. 3B) for passing 92 pull wires 92 therethrough. In some embodiments, wire holder 132 may serve as the aforementioned coupling element, which is coupled to the proximal end of pull wires 92, and is configured to by moved, by gear 111, along rotation axis 122 as described above. In some embodiments that were described above, boreholes 134 and respective rods 120 are configured to prevent rotation of the coupling element (in the present example wire holder 132)

when gear 111 rotates about rotation axis 122. In such embodiments, boreholes 134 and respective rods 120 are configured to prevent twisting of pull wires 92 when deflecting (and straightening) distal-end assembly 77.

Reference is now made back to FIGS. 2A and 2B above. Note that when retainers 60 are inserted into respective openings 61, pull wires 92 are rotating together with rotation mechanism 89 and tube 52, and therefore are not twisting around one another or around any other component of ENT tool 28. In some embodiments, when retainers 60 are inserted into respective openings 61, rods 120 (that are passing through boreholes 134) and panel 133 are rotating with rotation mechanism 89 when physician 24 rotates knob 54. In such embodiments, the entire structure of wire holder 132 rotates with rotation mechanism 89 when physician 24 rotates knob 54.

In some embodiments, when physician 24 rotates knob 66 for deflecting distal-end assembly 77, gear 111 rotates about rotation axis 122, however, boreholes 134 and respective rods 120 are configured to prevent rotation of wire holder 132, so as to prevent the aforementioned twisting of pull wires 92.

Reference is now made back to FIG. 3B. In some embodiments, wire holder 132 comprises a surface 131, which is typically circular, such that an inner surface (not shown) of gear 111, which is hollow, fits over and rotates about surface 131 when physician 24 rotates knob 66.

In some embodiments, wire holder 132 comprises a surface 135, which is an inner surface of panel 133 and is configured to make contact with gear 111. In such embodiments, when jagged section 113 makes contact with jagged surfaces 97 (as shown in inset 87 of FIG. 3A above), gear 111 moves in direction 117 and applies force to surface 135 so as to move wire holder 132 in direction 117 for deflecting distal end assembly 77. Note that when physician 24 controls gear 111 to move in direction 119, the inner force of the Nitinol™ acts as a spring that moves pull wires 92 in direction 119, so as to straighten distal-end assembly 77 to a non-deflective position.

The configuration of wire holder 132 is provided by way of example and may be simplified for the sake of conceptual clarity. In other embodiments, wire holder 132 may comprise additional boreholes and/or may have some of the boreholes shown in FIG. 3B combined together into a single borehole.

Figure 4:
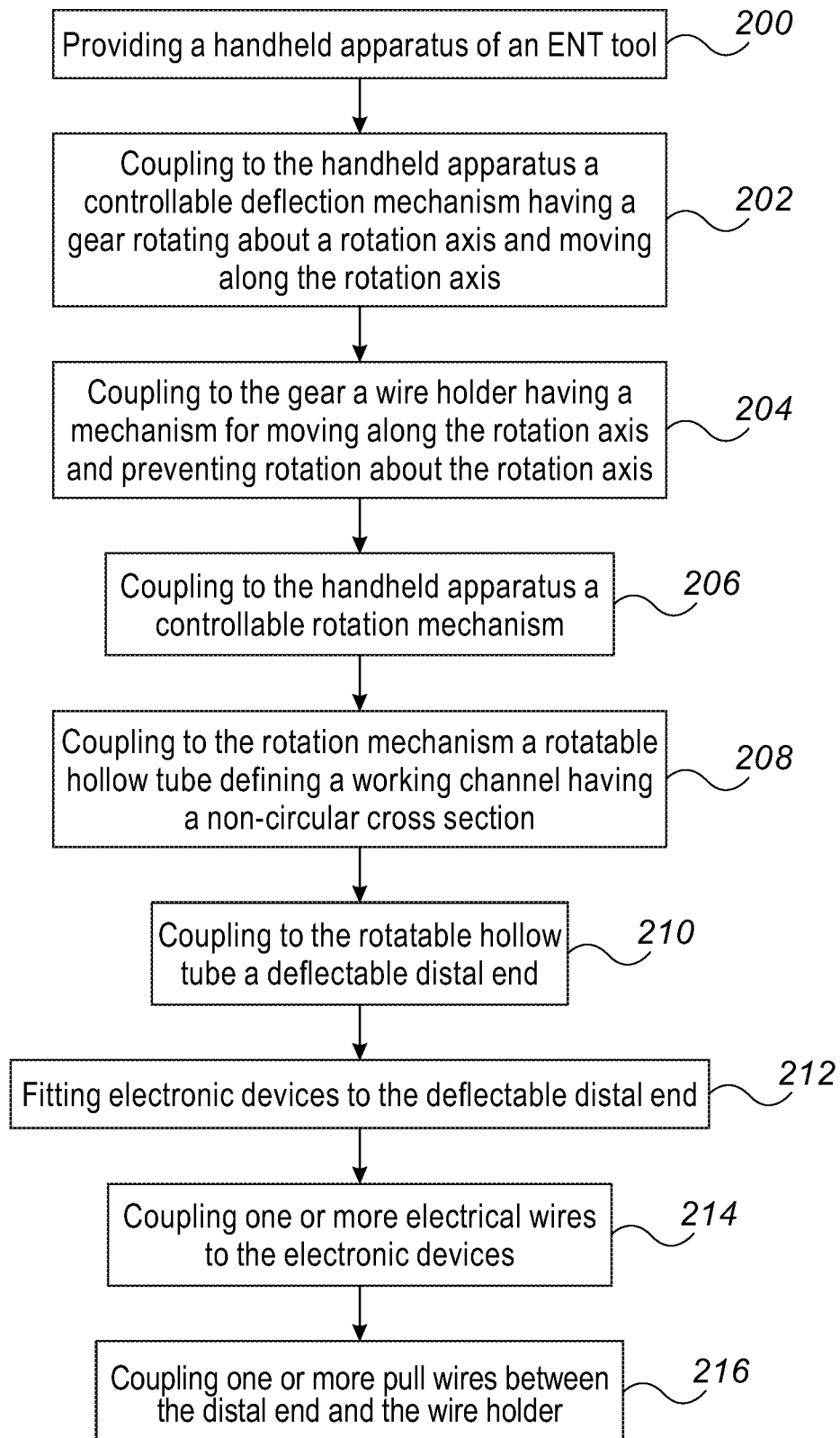
FIG. 4 is a flow chart that schematically illustrates a method for producing an ENT tool, in accordance with an embodiment of the present invention.

FIG. 4 is a flow chart that schematically illustrates a method for producing ENT tool 28, in accordance with an embodiment of the present invention. The method begins at a handheld apparatus providing step 200, with providing handheld apparatus 30 of ENT tool 28. At a deflection mechanism coupling step 202, deflection mechanism 99, which is controlled by knob 66, is coupled to handheld apparatus 30. As described in FIG. 3A above, deflection mechanism 99 comprises gear 111, which is hollow and is rotating about and moving along rotation axis 122.

At a wire holder coupling step 204, wire holder 132 is coupled to gear 111, for example by fitting wire holder 132 into the opening of hollow gear 111 as described in inset 87 of FIG. 3A above. In some embodiments, wire holder 132 has a mechanism for moving along rotation axis 122 and preventing rotation about rotation axis 122. In the present example described in FIG. 3B above, wire holder 132 has boreholes 134 for passing rods 120 therethrough, so as to enable moving wire holder 132 along rotation axis 122 and to prevent rotation of wire holder 132 about rotation axis 122. In some embodiments, the method for producing ENT tool 28 comprises fitting wire holder 132 within the hollow portion of gear 111 and inserting rods 120 into boreholes 134.

At a rotation mechanism coupling step 206, rotation mechanism 89, which is controlled by knob 54, is coupled to handheld apparatus 30. At a rotatable hollow tube coupling step 208 step, rotatable hollow tube 52 is coupled to rotation mechanism 89. In some embodiments, housing 53, which is coupled to tube 52 may be used for coupling between tube 52 and rotation mechanism 89. In such embodiments, rotation mechanism 89 comprises one or more protrusions 75, each of which configured to fit in a corresponding opening 73 of housing 53, so as to couple between tube 52 (using housing 53) and rotation mechanism 89. In some embodiments, the hollow section within tube 52 is defining working channel 62 having a non-circular cross section, as described in FIG. 2A above.

At a deflectable distal end coupling step 210, distal-end assembly 77 is coupled to the distal end of tube 52. At an electronic devices fitting step 212, position sensor 55 and one or more electronic devices 56 are fitted on distal-end assembly 77. At an electrical wires coupling step 214, one or more electrical wires, in the present example braid 90 of the electrical wires, is passed through working channel 62 and is coupled to position sensor 55 and to one or more electronic devices 56. During the procedure, a user of system 20, e.g., physician 24, may couple the proximal end of braid 90 to console 33 so as to enable exchanging of electrical power and electrical signals between console 33 and position sensor 55 and electronic devices 56, via the electrical wires of braid 90.

At a pull wires coupling step 216, one or more pull wires 92 are coupled between distal-end assembly 77 and wire holder 132. In the example of system 20, one or more pull wires 92 are passing through borehole 94 of wire holder 132, and are coupled to the outer surface of panel 133, as described in FIGS. 3A and 3B above.

In some embodiments, pull wires coupling step 216 concludes the method of FIG. 4. In other embodiments, the order of step 202-216 may differ from the order shown in FIG. 4. For example, (i) electrical wires coupling step 214 may be carried out before electronic devices fitting step 212, or (ii) electronic devices fitting step 212 may be carried out before distal end coupling step 210.

Moreover, the method steps of FIG. 4 are simplified for the sake of conceptual clarity, and the full production process of ENT tool 28 may comprise additional steps, such as but not limited to alignment between borehole 136 and working channel 62. The alignment may be carried out and tested, so that (i) physician 24 may easily insert one or more medical instruments 88 into the cavity of interest in the body of patient 22, and (ii) for placing braid 90 within ENT tool 28 and coupling the electrical wires thereof to position sensor 55 and to electrical devices 56.

Although the embodiments described herein mainly address ENT tools, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical tool, comprising:
   a distal end that is deflectable;
   at least a pull wire, having a first end coupled to the distal end of the medical tool and configured to be moved for deflecting the distal end; and
   a deflection assembly, which is coupled to a second end of at least the pull wire and is configured to control a deflection of the distal end, the deflection assembly comprising:
   a first gear having a first rotation axis; and
   a second gear, having a second rotation axis and comprising a jagged surface for integrating with the first gear, wherein the jagged surface is slanted relative to the second rotation axis, and wherein, when the first gear rotates, the second gear is configured to be rotated by the first gear and to move along the second rotation axis and deflect the distal end by moving the pull wire; wherein the second gear is hollow, and comprising one or more rods, which are parallel to the second rotation axis and traverse through the second gear so that the second gear is moved by the one or more rods along the second rotation axis.

2. The medical tool according to claim 1, wherein the second gear has a circumference comprising: (i) a first section having (a) a first thickness along the second rotation axis and (b) a first jagged section of the jagged surface extending therefrom, and (ii) a second section having (a) a second thickness along the second rotation axis, smaller than the first thickness and (b) a second jagged section of the jagged surface extending therefrom, and wherein, when the second gear is rotated:
   when the first jagged section is in contact with the first gear, the distal end is deflected by a first amount; and
   when the second jagged section is in contact with the first gear, the distal end is deflected by a second amount, smaller than the first amount.

3. The medical tool according to claim 1, and comprising a rotatable knob, which is coupled to the first gear and is configured to control the deflection by rotating the first gear.

4. The medical tool according to claim 1, and comprising a coupling element, which is coupled to the second end of at least the pull wire, and is configured to be moved, by the second gear, along the second rotation axis.

5. The medical tool according to claim 1, and comprising a hollow tube, disposed between the distal end and the deflection assembly, wherein the hollow tube defines a working channel therein for insertion of a medical instrument, through the distal end, which configured to be into a cavity of a patient body.

6. The medical tool according to claim 5, wherein the cavity comprises a nasal cavity in a head of the patient, and wherein the working channel is for inserting the medical instrument that is selected from a list consisting of: (a) a balloon, (b) a guidewire, (c) a pumping tube, (d) a surgical tool, (e) an ear-nose-throat diagnostics tool, (f) an ear-nose-throat treatment tool, and (g) any combination thereof.

* * * * *